United States Patent [19]
DeVries

[11] Patent Number: 6,102,038
[45] Date of Patent: Aug. 15, 2000

[54] EXHALATION VALVE FOR MECHANICAL VENTILATOR

[75] Inventor: Douglas F. DeVries, Redlands, Calif.

[73] Assignee: Pulmonetic Systems, Inc., Colton, Calif.

[21] Appl. No.: 09/080,327

[22] Filed: May 15, 1998

[51] Int. Cl.[7] ...................................................... A62B 9/02
[52] U.S. Cl. ................. 128/205.24; 128/204.23
[58] Field of Search .................. 128/205.24, 204.18, 128/204.21, 204.23, 205.19; 137/908, 114, 102

[56] References Cited

U.S. PATENT DOCUMENTS

| | | | |
|---|---|---|---|
| 5,694,922 | 12/1997 | Palmer | 128/202.27 |
| 5,740,796 | 4/1998 | Skog | 128/200.23 |
| 5,752,506 | 5/1998 | Richardson | 128/204.18 |
| 5,839,436 | 11/1998 | Fangrow, Jr. et al. | 128/205.24 |

*Primary Examiner*—Aaron J. Lewis
*Assistant Examiner*—Teena Mitchell
*Attorney, Agent, or Firm*—Klein & Szekeres, LLP

[57] ABSTRACT

An exhalation valve assembly for use in the mechanical ventilation of respiratory patients in which the PEEP valve and the exhalation valve are combined into a single valve mechanism, and which includes a wye in which the patient tube splits at equal angles into the ventilator tube and a tube closed off by the PEEP valve, so as to maintain the exhalation drive hose and the ventilator hose generally parallel, and avoid sharp angles in the air flow.

18 Claims, 4 Drawing Sheets

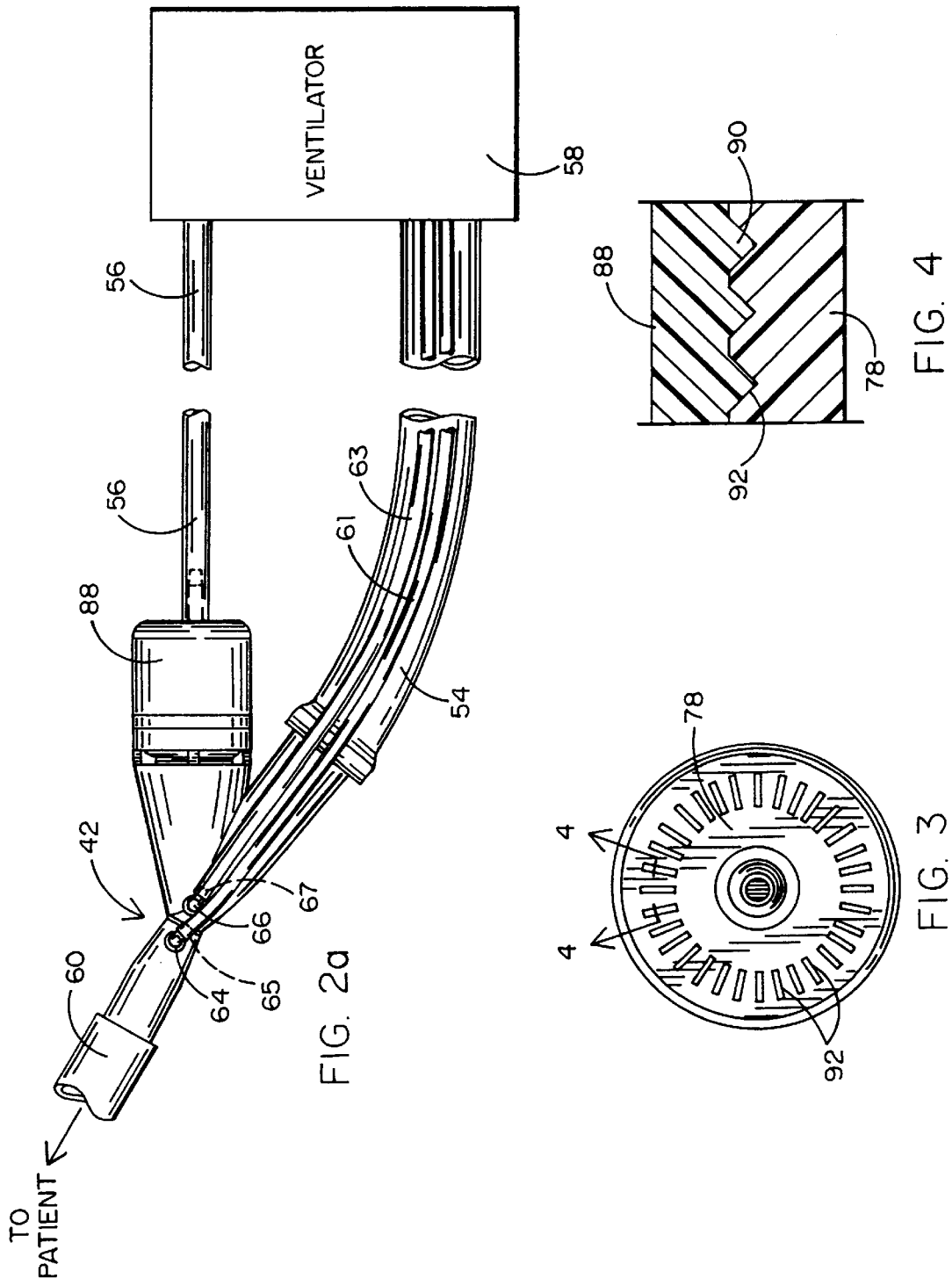

EXHALATION VALVE FOR MECHANICAL VENTILATOR

FIELD OF THE INVENTION

This invention relates to exhalation valves for mechanical ventilators, and more particularly to a low-profile adjustable exhalation valve assembly in which the closing function and the exhalation pressure control are combined in a single mechanism.

BACKGROUND OF THE INVENTION

Mechanical or positive pressure ventilators conventionally allow the patient to exhale through an exhalation valve attached to the air supply conduit which connects the ventilator to the patient. This valve is closed during inspiration by compressed air from the ventilator's exhalation drive output, but opens during the exhalation phase to allow the patient to exhale to atmosphere. For medical reasons, it is sometimes advantageous to provide an elevated back pressure above atmosphere during exhalation, known as positive end expiratory pressure (PEEP). This pressure is conventionally provided by a separate PEEP valve located downstream from and attached to the exhalation valve.

Prior art exhalation valve assemblies have typically been relatively large, complex and heavy. Because the exhalation valve assembly is attached to the patient's breathing tube, which is in turn affixed to the patient's trachea, the weight and bulk of the exhalation valve assembly can at the least create patient discomfort, and at the worst can lead to extubation or tissue damage.

It is therefore desirable to minimize the bulk and complexity of the exhalation valve assembly as well as to improve its efficiency. In the prior art, the separation of the exhalation valve from the PEEP valve in the exhalation valve assembly resulted in several right-angle corners in the air flow path that impeded air flow through the valve assembly to some degree.

SUMMARY OF THE INVENTION

The present invention provides an exhalation valve assembly which greatly reduces the bulk, complexity and weight of the assembly by combining the closing function and the PEEP control into a single unit. The inventive assembly permits substantial alignment of the patient, ventilator and exhalation drive tubes so as to occupy a minimum of space. Unnecessary flow impedances in the valve assembly are removed by eliminating sharp flow corners and positioning the flow-restricting obstruction needed for the flow sensing mechanism of the ventilator in substantial alignment with both the combined exhalation/PEEP valve and the ventilator tube.

BRIEF DESCRIPTION OF THE DRAWINGS

FIG. 1a is a longitudinal section of a prior art exhalation valve assembly;

FIG. 1b is a side elevational view of the prior art valve assembly of FIG. 1a;

FIG. 2a is an elevational view of the inventive exhalation valve assembly and its connections;

FIG. 3 is a section along line 3—3 of FIG. 2b;

FIG. 4 is a detail section along line 4—4 of FIG. 3; and

FIG. 5 is a detail section along line 5—5 of FIG. 1a.

DESCRIPTION OF THE PREFERRED EMBODIMENT

Figures 1A, 5:
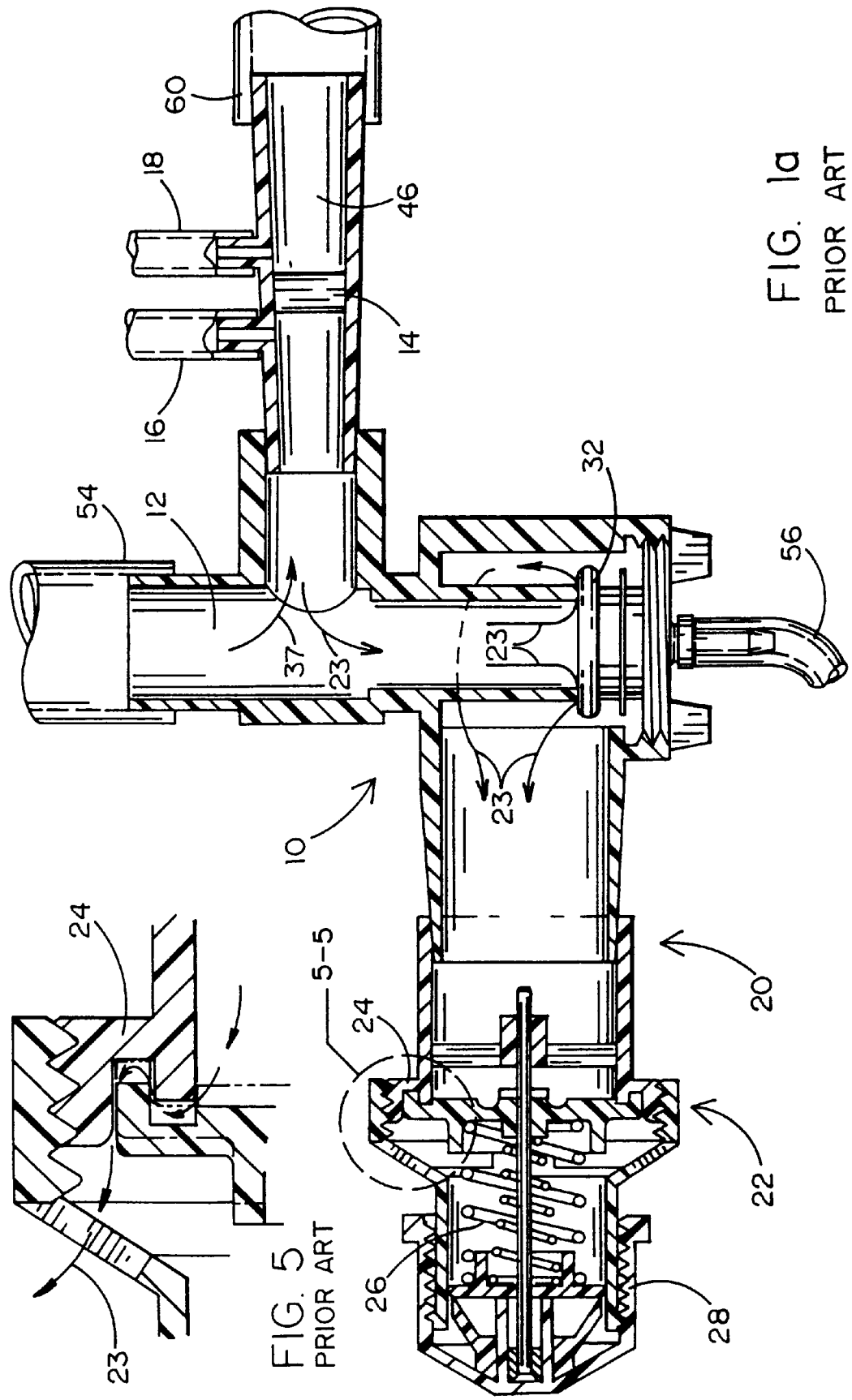

FIG. 1a shows a conventional prior art exhalation valve assembly 10. During inspiration, breathing gas flows from the ventilator 58 (FIG. 2a) through a ventilator tube 54, enters the exhalation valve assembly through port 12 connected to the ventilator tube 54, and flows into flow transducer tube 46 disposed at a right angle thereto. In the flow transducer tube 46, a flow restrictor 14 provides a sufficient pressure drop to cause a measurable pressure difference between the pressure sensor tube connections 16, 18. This pressure difference is used by the ventilator to measure air flow to and from the patient.

The PEEP valve assembly 20 extends at right angles to the port 12 and is offset from the flow transducer tube 46. The PEEP valve assembly 20 contains a valve element 22 which discharges exhaled air (arrows 23) in FIGS. 1a and 5 to atmosphere at 24 and operates against the adjustable bias of a spring 26. The bias of spring 26 can be adjusted by a screw cap 28. During inspiration, air flow into the PEEP valve assembly 20 is blocked by a separate balloon poppet exhalation valve 32 operated by air pressure from the exhalation drive of the ventilator transmitted through exhalation drive hose 56. Because the exhalation valve 32 extends at a right angle to the tube 46, the exhalation drive hose 56 and the ventilator hose 54 and flow sensor hoses 34, 36 extend substantially transversely to the tube 46 in opposite directions, which is awkward. Also, the two sharp angles between the tube 46 and the PEEP valve assembly 20 causes eddies which create resistance to flow thereby making both inspiration (flow arrow 37) and exhalation more difficult.

Figure 1B:
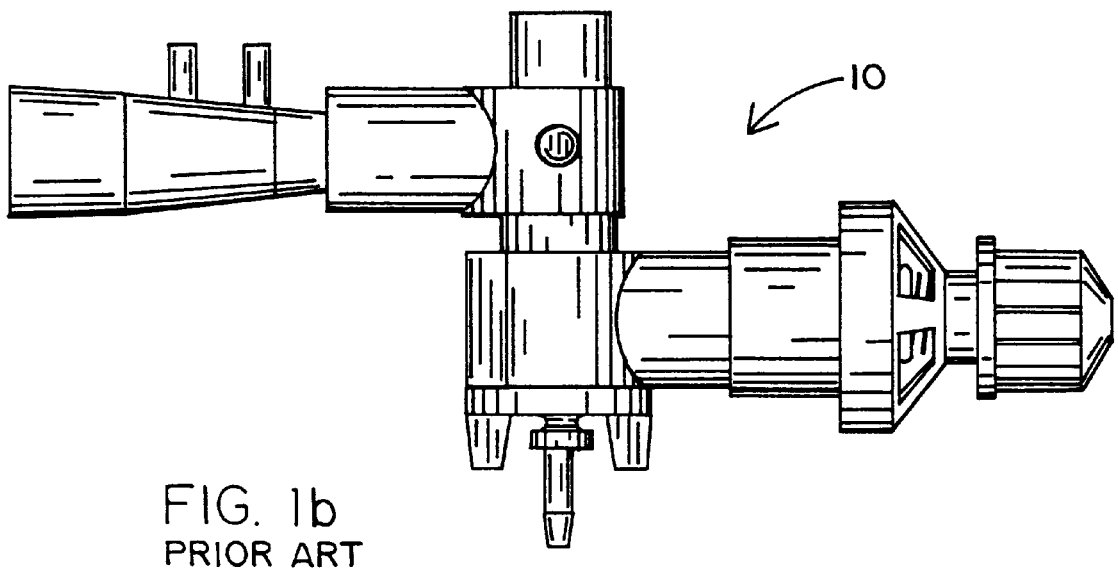
Figure 1C:
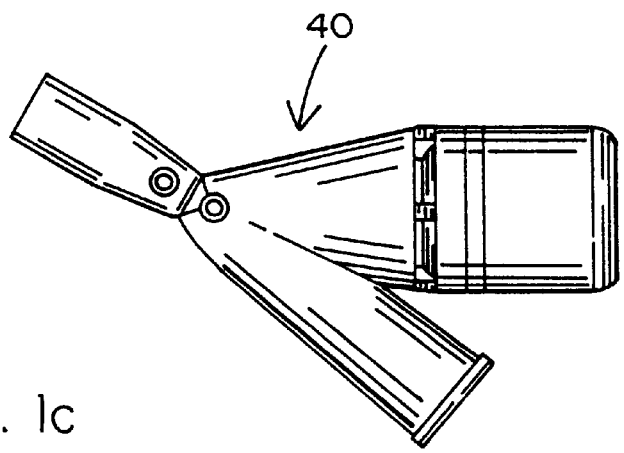
FIG. 1c is a side elevation of the inventive valve assembly drawn to the same scale as FIG. 1b.

The above-described prior art structure results in a relatively large and awkwardly shaped device, as is shown by the comparison FIGS. 1b and 1c which show, respectively, the prior art assembly 10 and the inventive assembly 40 drawn to the same scale.

Figure 2B:
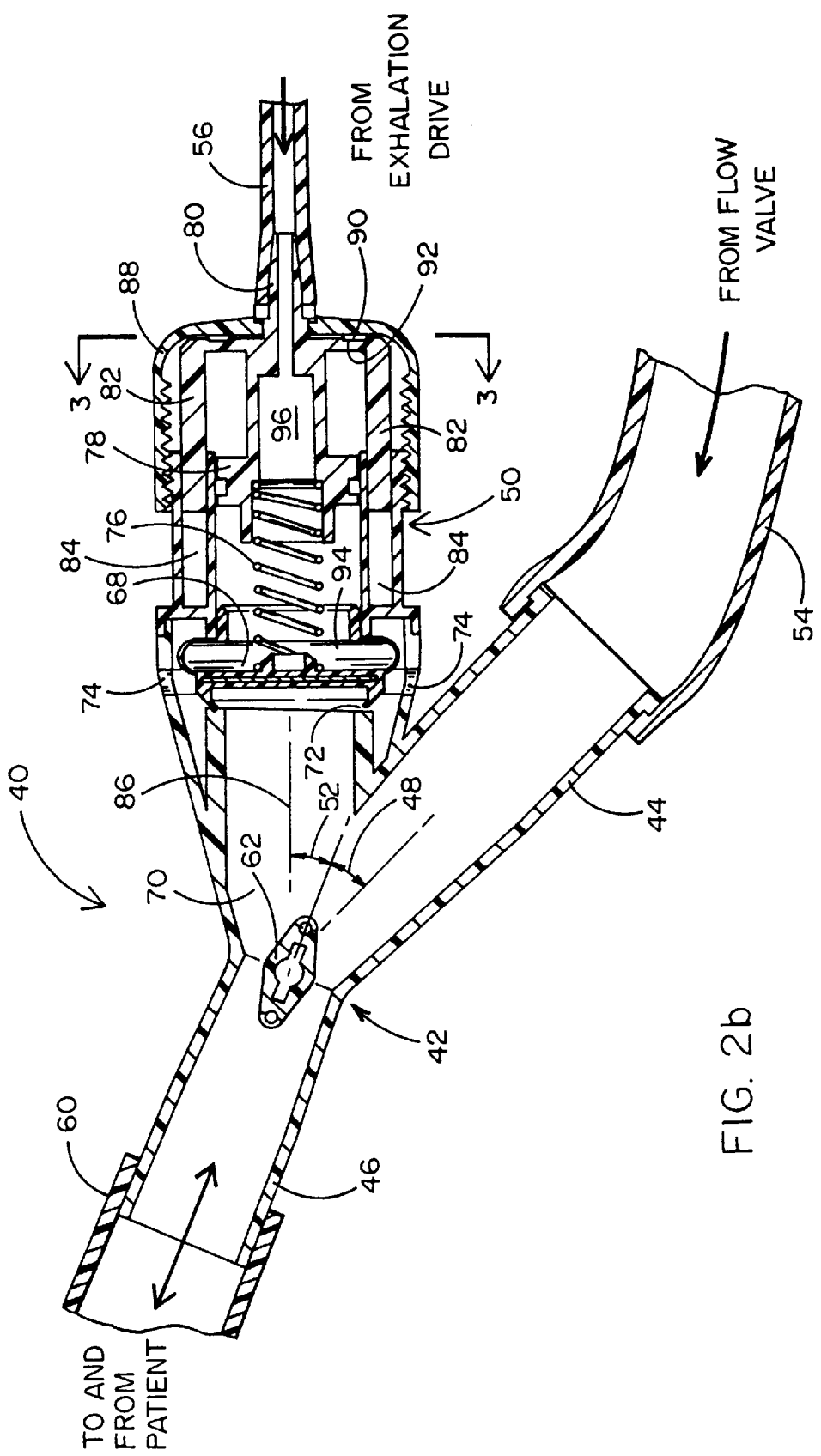
FIG. 2b is a longitudinal section of the inventive assembly.

FIGS. 2a and 2b show the inventive valve assembly 40. In the valve assembly 40, both the inspiration and exhalation air flow through a wye 42 in which the ventilator tube 44 extends at an angle 48 of about 22.5° to the flow transducer tube 46. On the opposite side of the axis of the flow transducer tube 46, the combined exhalation and PEEP valve assembly 50 extends at a like angle 52 of about 22.5° to the patient tube 46.

With the angle between the axes of ventilator tube 44 and combined exhalation and PEEP valve assembly 50 being thus about 45°, it will be seen in FIGS. 2a and 2b that the ventilator hose 54 and the exhalation drive hose 56 can be easily brought into close parallelism with each other on their way to the ventilator 58. Also, the hoses 54 and 56 will be in substantial alignment with the patient hose 60. The thin sensor hoses 61, 63 extending from the sensor fittings 64, 66 are easily oriented by elbow fittings 65, 67 to parallel the hoses 54, 56.

Referring now in more detail to FIG. 2b, a flow restrictor 62 is positioned at the throat of the wye 42. The flow restrictor 62 is elongated in the direction of the axis of the flow transducer tube 46 so as to pose the same obstruction to air flow toward the patient from ventilator tube 44 as to air flow from the patient into valve assembly 50. The sensor fittings 64, 66 (FIG. 2a) are mounted in the restrictor 62 on the axis of flow transducer tube 46.

The combined exhalation and PEEP valve assembly 50 itself combines the control and closing function into a single mechanism. The combined exhalation and PEEP valve assembly 50 includes a mushroom or balloon diaphragm exhalation valve 68 which, when open, allows air from conduit 70 to escape to atmosphere through annulus 72 and slots 74. The valve 68 is biased into the closed position by a spring 76 which is held in a movable seat 78. The seat 78 is formed integrally with the connector 80 for the exhalation drive hose 56. Also integrally formed with the spring seat 78 are guide arms 82 which slide axially in channels 84 but are held against rotation about the axis 86 by the channels 84.

A cap 88 screwthreadedly engages the outside of channels 84 and can be moved axially of the combined exhalation and PEEP valve assembly 50 by rotary movement about the axis 86. Accidental movement of the cap 88 is prevented by teeth 90 (FIG. 4) on the inside of the cap 88 which engage complementary radial grooves 92 on the upper surface of spring seat 78. Thus, the spring bias of the PEEP function (and thereby the positive end exhalation pressure seen by the patient) can be adjusted as necessary.

In accordance with the invention, the PEEP control valve 68 serves also as the exhalation closing function. This is accomplished by exposing the chamber 94 of valve 68 to air pressure from the exhalation drive through hose 56 and passage 96. When the exhalation drive of the ventilator 58 pressurizes the chamber 94, the valve 68 of FIG. 2b is closed and can be opened neither by exhalation nor by the pressure of the inspiration flow.

It is understood that the exemplary exhalation valve assembly for mechanical ventilators described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. An exhalation valve assembly for a mechanically ventilated patient, comprising:
    a) a first conduit having a first end configured for connection to a patient, and a second end;
    b) a second conduit having a first end configured for connection to a ventilator, and a second end in fluid communication with the second end of the first conduit;
    c) a third conduit having a first end in fluid communication with the first and second conduits, and a second end openable to atmosphere;
    d) a valve located adjacent the second end of the third conduit and biased in the closed position so as to controllably open the second end of the third conduit; and
    e) a fourth conduit substantially coaxial with the valve and said third conduit and configured for connection to a source of exhalation drive pressure for communicating the exhalation drive pressure to the valve;
    f) the valve comprising:
        a spring engaged by a rotatable cap and an axially movable spring seat arranged to vary the bias of the spring by rotation of the cap; and
        a chamber exposed to exhalation drive pressure from said fourth conduit and being arranged to lock the valve closed by the exhalation drive pressure.

2. The valve assembly of claim 1, in which each of said first, second, and third conduits has an axis, the axes of said second and third conduits being disposed at an acute angle on opposite sides of the axis of said first conduit.

3. The valve assembly of claim 2, in which said angle is substantially 22.5°.

4. The valve assembly of claim 1, further comprising:
    h) a flow restrictor positioned in said first conduit at the junction thereof with said second and third conduits;
    i) said flow restrictor being elongated in a direction axial of said first conduit.

5. The valve assembly of claim 1, in which said axially movable spring seat is held against rotation about the axis of said third and fourth conduits.

6. An exhalation valve assembly for a mechanical ventilator that provides a flow of inspiratory gas to a patient during inspiration and that provides an exhalation drive pressure during inspiration, the exhalation valve assembly comprising:
    a) a first conduit having a first end configured to receive exhaled gas from a patient, and a second end;
    b) a second conduit having a first end configured to receive inspiratory gas from a mechanical ventilator, and a second end that is in fluid communication with the second end of the first conduit;
    c) a third conduit having a first end in fluid communication with the first and second conduits, a second end that is openable to atmosphere;
    d) a fourth conduit having a first end configured to receive the exhalation drive pressure during inspiration, and a second end; and
    d) a combined exhalation and PEEP valve located so as to control the flow of exhaled gas through the second end of the third conduit, the combined exhalation and PEEP valve comprising:
        a valve element exposed to the exhalation drive pressure from the fourth conduit and biased toward a closed position against the second end of the third conduit so as to control the flow of exhaled gas therethrough, whereby the valve element is closed against the second end of the third conduit in response to the exhalation drive pressure; and
        means for adjusting the bias applied to the valve element.

7. The exhalation valve assembly of claim 6, wherein the fourth conduit is substantially coaxial with the third conduit.

8. The exhalation valve assembly of claim 6, wherein the valve element comprises a diaphragm having a first side disposed against the second end of the third conduit and a second side exposed to the exhalation drive pressure.

9. The exhalation valve assembly of claim 8, wherein the combined exhalation and PEEP valve further comprises a spring having a first end engaged against the second side of the diaphragm and a second end, and wherein the means for adjusting the bias comprises:
    an axially-movable spring seat engaged against the second end of the spring; and
    means for adjustably moving the spring seat axially.

10. The exhalation valve assembly of claim 9, wherein the means for adjustably moving the spring seat comprises a rotatable cap coupled to the spring seat for moving the spring seat axially in response to the rotation of the cap.

11. A device for conducting inspiratory gas from a mechanical ventilator to a patient, and for conducting exhaled gas from the patient, comprising:
    a) a first conduit having a first end configured to receive exhaled gas from a patient, a second end, and a first axis defined between the first and second ends of the first conduit;

b) a second conduit having a first end configured to receive inspiratory gas from a mechanical ventilator, a second end communicating with the second end of the first conduit, and a second axis defined between the first and second ends of the second conduit that defines an acute angle with the first axis on a first side of the first axis;

c) a third conduit having a first end communicating with the second end of the first conduit and the second end of the second conduit, a second end that is openable to atmosphere, and a third axis defined between the first and second ends of the third conduit that defines an acute angle with the first axis on a second side of the first axis opposite the first side, whereby the second end of the second conduit and the first end of the third conduit are joined to the second end of the first conduit at a "Y"-shaped juncture; and d) a differential flow sensor element located at the "Y"-shaped juncture.

12. The device of claim 11, wherein the differential flow sensor element comprises a flow restrictor having an elongated dimension substantially aligned with the first axis.

13. The device of claim 12, wherein the flow restrictor has first and second ends, each end including means for the attachment of a sensor tube.

14. A combination exhalation and PEEP valve for a mechanical ventilator that provides a flow of inspiratory gas to a patient during inspiration and that provides an exhalation drive pressure during inspiration, the valve comprising:

a first conduit configured to conduct exhaled gas from a patient during exhalation, the first conduit having an end openable to atmosphere;

a valve element disposed adjacent the end of the first conduit;

biasing means for biasing the valve element toward a closed position against the end of the first conduit so as to controllably open the end of the first conduit; and a second conduit substantially coaxial with the valve element and the first conduit and configured for communicating the exhalation drive pressure to the valve element.

15. The combination exhalation and PEEP valve of claim 14, wherein the valve element is closed against the open end of the first conduit in response to the exhalation drive pressure, and wherein the biasing means includes means for adjusting the bias applied to the valve element.

16. The combination exhalation and PEEP valve of claim 14, wherein the valve element comprises a diaphragm having a first side disposed against the open end of the first conduit and a second side exposed to the exhalation drive pressure.

17. The combination exhalation and PEEP valve of claim 16, wherein the biasing means comprises a spring having a first end engaged against the second side of the diaphragm and a second end, and wherein the means for adjusting the bias comprises:

an axially-movable spring seat engaged against the second end of the spring; and means for adjustably moving the spring seat axially.

18. The combination exhalation and PEEP valve of claim 17, wherein the means for adjustably moving the spring seat comprises a rotatable cap coupled to the spring seat for moving the spring seat axially in response to the rotation of the cap.

* * * * *